US011033199B2

(12) United States Patent
Johnson et al.

(10) Patent No.: US 11,033,199 B2
(45) Date of Patent: Jun. 15, 2021

(54) ECHO-PLANAR IMAGING MAGNETIC RESONANCE ELASTOGRAPHY PULSE SEQUENCE

(71) Applicant: THE BOARD OF TRUSTEES OF THE UNIVERSITY OF ILLINOIS, Urbana, IL (US)

(72) Inventors: Curtis L. Johnson, Urbana, IL (US); Bradley Sutton, Savoy, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 1127 days.

(21) Appl. No.: 15/193,171

(22) Filed: Jun. 27, 2016

(65) Prior Publication Data

US 2016/0374586 A1 Dec. 29, 2016

Related U.S. Application Data

(60) Provisional application No. 62/185,770, filed on Jun. 29, 2015.

(51) Int. Cl.
| | |
|---|---|
| *A61B 5/055* | (2006.01) |
| *G01R 33/48* | (2006.01) |
| *G01R 33/563* | (2006.01) |
| *A61B 5/00* | (2006.01) |
| *G01R 33/561* | (2006.01) |

(52) U.S. Cl.
CPC ............ *A61B 5/055* (2013.01); *A61B 5/4244* (2013.01); *G01R 33/56358* (2013.01); *A61B 5/0037* (2013.01); *G01R 33/5616* (2013.01)

(58) Field of Classification Search
CPC ..... A61B 5/055; A61B 5/4244; A61B 5/0037; G01R 33/56358; G01R 33/5616
See application file for complete search history.

(56) References Cited

U.S. PATENT DOCUMENTS

| | | | | |
|---|---|---|---|---|
| 5,998,996 A | * | 12/1999 | Bernstein | ......... G01R 33/56581 324/307 |
| 8,217,649 B2 | | 7/2012 | Bolster, Jr. | |
| 9,035,652 B2 | * | 5/2015 | Nishihara | .............. A61B 5/055 324/309 |

(Continued)

OTHER PUBLICATIONS

Johnson, C. L. Imaging the local mechanical properties of the brain with high-resolution magnetic resonance elastography, 2013, (Doctoral dissertation, University of Illinois at Urbana-Champaign), pp. 1-117 (Year: 2013).*

(Continued)

*Primary Examiner* — Patricia J Park
(74) *Attorney, Agent, or Firm* — Guntin & Gust, PLC; Robert Gingher (57) ABSTRACT

Magnetic resonance elastography (MRE) is an imaging technique for estimating the stiffness of tissues non-invasively. Shear waves are generated via external mechanical actuation and the tissue imaged with a specially designed MR pulse sequence. The resulting images are used to calculate the underlying properties. The application provides methods for acquiring MRE data using a single shot, echo planar imaging readout. The purpose of the developed sequence is to acquire MRE data using a single-shot, echo-planar imaging readout, avoiding to need for off-line image processing.

20 Claims, 8 Drawing Sheets

(56) References Cited

U.S. PATENT DOCUMENTS

| | | | |
|---|---|---|---|
| 2006/0012367 A1* | 1/2006 | Meaney | A61B 5/0035 |
| | | | 324/315 |
| 2007/0167729 A1* | 7/2007 | Mistretta | G01R 33/4824 |
| | | | 600/410 |
| 2012/0269415 A1 | 10/2012 | Glaser et al. | |
| 2014/0107467 A1 | 4/2014 | Felmlee et al. | |

OTHER PUBLICATIONS

Schuh, A., Impatient MRI Toolset Documentation. (Feb. 26, 2015). Retrieved Apr. 22, 2019. pp. 1-9 (Year: 2015).*

"Yang et al.," "Optimizing Abdominal MR Imaging: Approaches to Common problems," RadioGraphics vol. 30 No. 1, pp. 185-199, Jan. 2010.*

Rosen, Bruce et al., "MR Image Encoding", HST.584J: Magnetic Resonance Analytic, Biochemical, and Imaging Techniques, 2006.

* cited by examiner

ECHO-PLANAR IMAGING MAGNETIC RESONANCE ELASTOGRAPHY PULSE SEQUENCE

CROSS-REFERENCE TO RELATED APPLICATIONS

This application claims the benefit of U.S. Provisional Patent Application Ser. No. 62/185,770, entitled Echo-Planar Imaging Magnetic Resonance Elastography Pulse Sequence, filed Jun. 29, 2015, which is incorporated by reference herein in its entirety.

FIELD OF THE DISCLOSURE

The present disclosure generally relates to magnetic resonance imaging (MRI), and more particularly to magnetic resonance elastography (MRE).

BACKGROUND

The application of MRE in the study of the brain has received significant impetus in recent years from studies that indicate that the mechanical properties of brain parenchyma are very sensitive to neurological disease state. Significant scientific and clinical interest in MRE exists due to the potential for distinguishing specific microstructural tissue characteristics through the mechanical properties, which is already demonstrating initial validation from animal models and histology. While previous studies found success in a research setting, the clinical application of brain MRE has been limited by the inability to rapidly capture the three dimensional, full vector MRE displacement field.

BRIEF DESCRIPTION OF THE DRAWINGS

The features, objects and advantages other than those set forth above will become more readily apparent when consideration is given to the detailed description below. Such detailed description makes reference to the following drawings, wherein.

DETAILED DESCRIPTION

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise. "Comprising" means "including"; hence, "comprising A or B" means "including A" or "including B" or "including A and B." All references cited herein are incorporated by reference.

The disclosure may be further understood by the following non-limiting examples. All references cited herein are hereby incorporated by reference to the extent not inconsistent with the disclosure herewith. Although the description herein contains many specificities, these should not be construed as limiting the scope of the disclosure but as merely providing illustrations of some of the presently preferred embodiments of the disclosure. For example, thus the scope of the disclosure should be determined by the appended aspects and their equivalents, rather than by the examples given.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

Magnetic Resonance Elastography (MRE) is a rapidly developing technology for quantitatively assessing the mechanical properties of tissue. The technology can be considered to be an imaging-based counterpart to palpation, commonly used by physicians to diagnose and characterize diseases. The success of palpation as a diagnostic method is based on the fact that the mechanical properties of tissues are often dramatically affected by the presence of disease processes such as cancer, inflammation, and fibrosis. MRE obtains information about the stiffness of tissue by assessing the propagation of mechanical waves through the tissue with a special magnetic resonance imaging (MRI) technique. The technique essentially involves three steps: generating shear waves in the tissue, acquiring MRIs depicting the propagation of the induced shear waves, and processing the images of the shear waves to generate quantitative maps of tissue stiffness, called elastograms.

MRE may be used for the clinical assessment of patients with chronic liver diseases. MRE is emerging as a safe, reliable and noninvasive alternative to liver biopsy for staging hepatic fibrosis. MRE is also being investigated for application to pathologies of other organs including the brain, breast, blood vessels, heart, kidneys, lungs and skeletal muscle.

Through the use of a rapid motion encoding gradient (MEG) sequence that is robust and flexible, MEG can be more widely adopted into clinical practice. The current disclosure provides a single shot, spin echo MEG sequence developed for acquiring MRE data. The MEG sequence is used to acquire MRE data using a single-shot, echo-planar imaging (EPI) readout. This MEG sequence takes advantage of image reconstruction software available on clinical MRI scanners, and avoids the need for extensive off-line image processing. The MEG sequence measures three dimensional, full vector displacement fields in organs or tissues of the body. The methods described herein may be used to acquire MRE data from various organs of the body, including, but not limited to brain, breast, blood vessels, heart, liver, kidneys, lungs and skeletal muscle.

The methods find utility in providing rapid MRE measurements for better detection of diseased states or other pathologies within tissue. The use of this MEG sequence can allow medical practitioner to make more accurate diagnoses and prognoses to direct improved medical treatment plans.

The system for MRI of mechanically agitated tissue comprises an external wave generator for generating mechanical waves for transmission through patient anatomy. A spatially selective gradient generator generates a spatially selective magnetic field for selection of a volume comprising a slice of an anatomical region of interest. An RF pulse generator generates an RF pulse for exciting nuclei magnetic moments in a particular volume comprising the anatomical region of interest selected using the spatially selective magnetic field. A motion encoding gradient generator generates a motion encoding gradient magnetic field concurrently with the acquisition of an MRI signal generated in response to the excitation. The motion encoding gradient magnetic field is synchronized with generation of the mechanical waves. A data processor processes the MRI signal generated in response to the excitation and resulting from excited nuclei responsive to the motion encoding gradient magnetic field, to detect the motion of the tissue from mechanical agitation as waves are propagated through the patient anatomy.

Figure 1:
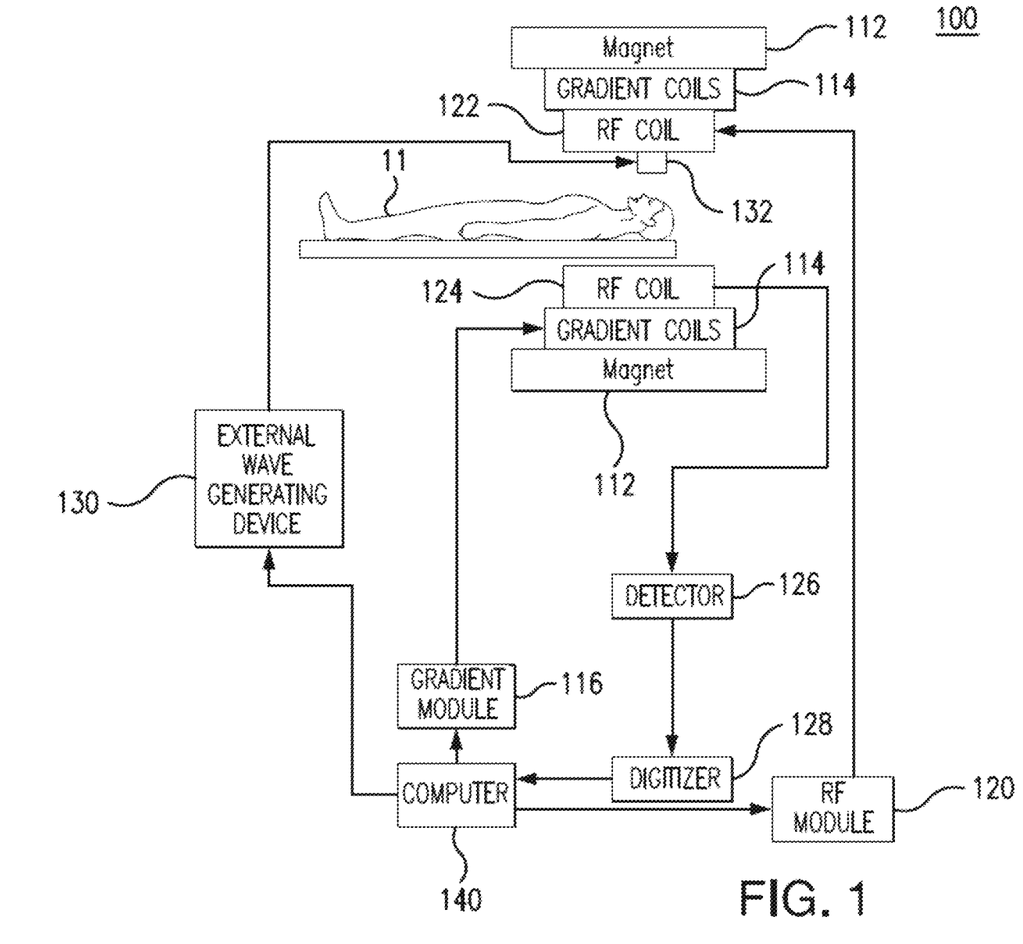
FIG. 1 is a block diagram illustrating a MRE system.

FIG. 1 is a block diagram illustrating a system 100 for use in MRI of mechanically agitated tissue. In system 100, a magnet 112 creates a static base magnetic field in the patient tissue 11 to be imaged while the patient is positioned on a table. Within the magnet system are gradient coils 114 for producing position dependent magnetic field gradients superimposed on the static magnetic field. Gradient coils 114, in response to gradient signals supplied thereto by a gradient control module 116, produce position dependent and shimmed magnetic field gradients in three orthogonal directions and generates pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient tissue 11.

A radio frequency (RF) module 120 provides RF pulse signals to an RF coil 122, which in response produces magnetic field pulses that excite the spins of the protons in the imaged body tissue.

An external wave generator 130 generates mechanical waves for transmission through patient tissue 11 by a transducer 132 and a spatially selective gradient generator generates a spatially selective magnetic fields for selection of a volume comprising an anatomical region of interest. Gradient control module 116 in conjunction with RF module 120 as directed by computer 140, control slice-selection, phase-encoding, readout gradient magnetic fields, radio frequency transmission, and magnetic resonance signal detection, to acquire magnetic resonance signals representing planar slices of patient tissue 11.

In response to applied RF pulse signals, RF coils 124 receive MRI signals, i.e., signals from the excited protons within the body as they return to an equilibrium position established by the static and gradient magnetic fields. The MRI signals are detected by a detector 126 (comprising a preamplifier and amplifier), the MRI signals are then filtered by an analog low-pass filter (the pass band of which is controlled directly or indirectly by the pulse sequence and computer 140), converted into digital signals by a digitizer 128 and provided to the computer 140. Alternatively, a digital filter may be used instead of, or in conjunction with, an analog low-pass filter. The MRI signals are detected and processed by a detector within RF module 120 to provide image representative data to an image data processor in computer 140.

Computer 140 includes a graphical user interface (GUI) enabling user interaction with the computer 140 via a user data entry device and enabling user modification of magnetic resonance imaging signals in substantially real time. Computer 140 uses information stored in an internal database to process the detected MRI signals in a coordinated manner to generate high quality images of a selected planar slice (or slices) of the body and adjust other parameters of system 100. Computer 140 similarly generates graphical representations of vector displacement fields in organs or tissues of the body, such as the brain or liver or muscle, in response to mechanical waves transmitted through patient anatomy. Displacement fields can also be measured in soft materials and other objects capable of being imaged in an MRI scanner. The resulting displacement fields are of sufficient quality for processing. The displacement fields represent a quantitative estimate of the sheer modulus of the tissue, i.e., Young's modulus of elasticity. The stored information comprises predetermined pulse sequence and magnetic field gradient and strength data as well as data indicating timing, orientation and spatial volume of gradient magnetic fields to be applied in imaging, as explained in further detail below. Generated images and data are presented on a display.

Figure 2:
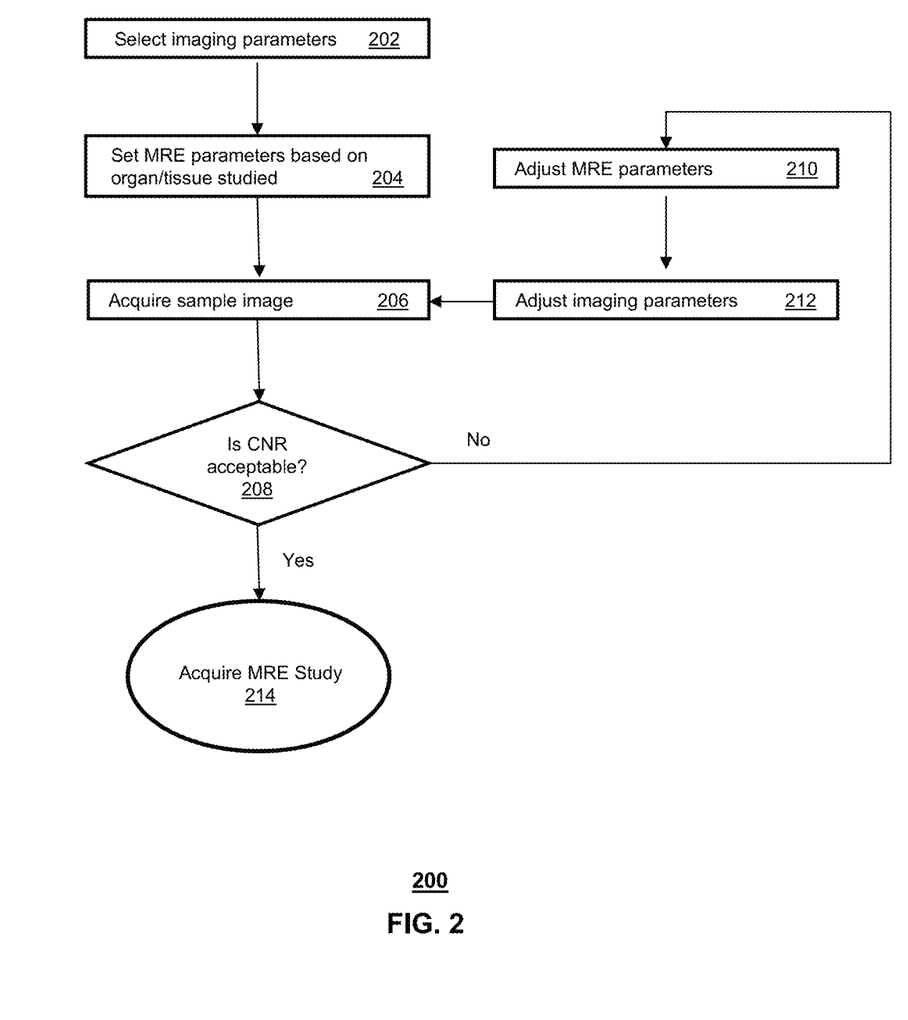
FIG. 2 is a flow chart illustrating a method of MRE.

FIG. 2 is a flow chart illustrating a method 200 of MRE. As shown in FIG. 2, in step 202, imaging parameters are selected. The imaging parameters include image resolution, number of slices, bandwidth, parallel imaging, echo time (TE), and repetition time (TR).

Image resolution is defined by the size of each voxel in the image slice matrix. Since voxels are three dimensional rectangular solids, the resolution is frequently different in the three different directions. The size of the voxel, and therefore the resolution, depends on matrix size, the field-of-view (FOV), and the slice thickness. The matrix size is the number of frequency encoding steps, in one direction; and the number of phase encoding steps, in the other direction of the image plane.

Bandwidth (BW) is the range of frequencies associated either with RF-excitation (transmitter bandwidth, tBW) or signal reception (receiver bandwidth, rBW).

Parallel imaging is a method for accelerating the acquisition of MRI data. Parallel imaging works by acquiring a reduced amount of k-space data with an array of receiver coils. These undersampled data can be acquired more quickly, but the undersampling leads to aliased images. One of several parallel imaging algorithms can then be used to reconstruct artifact-free images from either the aliased images (SENSE-type reconstruction) or from the undersampled data (GRAPPA-type reconstruction). The advantages of parallel imaging in a clinical setting include faster image acquisition, which can be used, for instance, to shorten breath-hold times resulting in fewer motion-corrupted examinations.

Echo time (TE) is the time between the application of radiofrequency excitation pulse and the peak of the echo signal induced in the coil. TE is measured in milliseconds. T2-relaxation refers to the progressive dephasing of spinning dipoles following the 90° RF excitation pulse, as seen in a spin-echo sequence due to tissue-particular characteristics, primarily those that affect the rate of movement of protons, most of which are found in the hydrogen nuclei of water molecules. This is alternatively known as spin-spin relaxation. The effect that T2-relaxation has on the degradation of the echo signal is controlled by TE.

Repetition time (TR) is the time from the application of an excitation pulse to the application of the next pulse. TR, typically expressed measured in milliseconds, determines how much longitudinal magnetization recovers between each pulse.

In step 204, a set of magnetic resonance elastographic parameters (MRE parameters) are selected based on the organ or tissue under study. After determining the organ or tissue under study, and setting desired imaging parameters, the MRE parameters are determined. The MRE parameters include: encoding directions, MEG polarity, mechanical excitation frequency, number of phase offsets, fractional encoding factor, MEG shape and MEG strength.

The motion encoding directions correspond to the magnetic field gradient directions that are applied to a patient during an MRI. The magnetic field gradients include a slice-selection gradient magnetic field, a phase-encoding gradient magnetic field, and a readout gradient magnetic field. The motion encoding direction can include one of the three magnetic field gradient directions (i.e., slice-selection, phase encode, or readout directions), or may include all three directions, sequentially. The use of more encoding directions increases the acquisition time. Acquiring all directions of motion results in the recovery of a full vector three dimensional displacement field.

MEG polarity can be in one direction (positive) or with an additional reversed polarity direction (positive/negative). A reversed polarity gradient removes background phase, which increases image contrast. However, a reversed polarity gradient requires additional data acquisition time, which takes twice as long.

The mechanical excitation frequency is the frequency used for mechanical agitation, i.e., agitation that vibrates the tissue under study, as applied by the transducer 132 shown in FIG. 1. The frequency is chosen to achieve a desired wavelength and penetration through the body to sufficiently effect desired tissue deformation within the elastic range of the tissue. This tissue deformation occurs in all three spatial dimensions and is described by a full vector displacement field. Generally, the mechanical excitation frequency is in the range of 25-100 Hz, which covers the majority of applications in the human body. In particular, the frequency chosen is based on the organ under study. For example, for brain MRE, a preferred mechanical excitation frequency is 50 Hz, although frequencies in the range of 50-60 Hz were found to be suitable. This frequency range is also suitable for liver MRE, and most other human tissue. Selection of the mechanical excitation frequency determines characteristics of the MEG sequence. For instance, the mechanical excitation frequency is used to define the base MEG length in the MEG sequence. Typically, the base MEG length is an amount of time equivalent to the period of mechanical vibration. For example, given a 50 Hz mechanical excitation frequency, the base MEG length will be 20 ms, as this is the period of vibration.

The mechanical excitation frequency also determines the spacing between phase offsets in the MEG sequence. Encoding gradients on either side of the RF refocusing pulse are designed to capture in-phase motion of the tissue, and thus are separated in time by either a half or full period of vibration. Phase offsets are a number of equally spaced data points acquired during a single cycle of mechanical vibration. The data points are used to reconstruct the deformation patterns of the tissue over a cycle of vibration. Recovery of complex displacement fields are improved if more phase offsets are used, however this increases the acquisition time.

The fractional encoding factor changes the length of the MEGs relative to the base MEG length. The fractional encoding factor is applied to the base MEG length to shorten the gradient length. A shorter MEG length results in a lower encoding sensitivity, but also permits a shorter echo time (TE). A shorter TE means less of the MR signal has relaxed when the echo is recorded. The echo signal magnitude experiences an exponential decay from the RF excitation pulse to the echo time, governed by the T2-relaxation value of the tissue. Thus, a shorter echo time results in a greater echo signal strength. When a tissue has a short T2-relaxation time, the decay of the echo signal is more prominent, thereby increasing the importance of having a shorter echo time to obtain a stronger echo signal. Thus, TE may be an important consideration when imaging different tissues. The range of possible fractional encoding factors is between 0.2 and 1.0.

Generally, the MEG shape changes sensitivity to motion imparted by the mechanical excitation, or due to any nuisance motion (e.g., fluid flow in the tissue under study). The MEG shape may either be bipolar (1-1) or flow-compensated (1-2-1). Bipolar gradients have two, equal-length lobes. A bipolar gradient shape has more sensitivity to motion at low fractional encoding factors. Flow-compensated gradients have three lobes, with the middle lobe being twice as long as the other two side lobes. Flow-compensated gradients are not optimal when used with low fractional encoding factors.

MEG strength defines the amplitude of the applied MEGs, and directly affects the encoding sensitivity. In most scenarios, the system maximum will be used. A lower MEG strength can be used to overcome phase wrapping, which would prevent analysis of the data without a phase unwrapping procedure, which in turn can lead to uncertain results.

As mentioned above, the MRE parameters are initially chosen based on the organ or tissue of interest from a pre-defined set of parameters chosen to result in a likely successful MRE study. An example of a pre-defined parameter set for a brain includes: three encoding directions; reversed polarity gradient; eight phase offsets; 50 Hz vibration frequency; 1.0 fractional encoding; flow-compensated gradient shape; maximum gradient strength. An example of a pre-defined parameter set for a liver includes: one encoding direction (Z); reversed polarity gradient; three phase offsets; 60 Hz vibration frequency; 0.4 fractional encoding; bipolar gradient shape; and maximum gradient strength.

Next, in step 206, the parameters are used to generate a MEG sequence used to acquire a sample image so that a contrast-to-noise ratio (CNR) measurement can be obtained. The CNR is equal to the product of contrast and the signal to noise ratio (SNR) of the acquired image data. The CNR determines whether a successful MRE study can be conducted. The CNR is calculated from the sample magnetic resonance image.

Next, in step 208, the CNR is compared to a target CNR. The target CNR is a predetermined level for MRE experiments that relates the strain of the measured displacement field to the noise. For example, the target CNR value may be 3. If the CNR exceeds the target CNR, then the process continues to step 214. If the target CNR is not met, then the process continues to step 210.

In step 210, the MRE gradient parameters are updated to improve the CNR. The MRE gradient parameter adjustments are based on measured encoding sensitivity and estimated SNR from T2-relaxation from the TE and known tissue properties. The motion encoding sensitivity is based on total MEG length (frequency and fractional encoding), MEG strength, and MEG shape, as described above. Longer gradients have a greater sensitivity and will yield images having a higher contrast, and improved CNR. To improve CNR, for example, the fractional encoding factor can be increased, which in turn will increase the MEG length, and correspondingly the contrast. However, increasing MEG length may also require an increased TE, as explained further below with respect to FIG. 4. Increasing TE will reduce the SNR, which has a reduction effect on CNR. However, this procedure will still improve the CNR since contrast is proportional to MEG length, while the SNR follows an exponential decay, based on TE.

In step 212, imaging parameters are adjusted. The echo time (TE) can be updated based on total MEG length (which depends on vibration frequency and fractional encoding, as described above) and spacing between phase offsets in the MEG sequence (which depends on vibration frequency, as detailed above). As noted above, a shorter TE yields images having a higher SNR. The process then repeats back to step 206

In step 214, after the target CNR is reached, the MRE study is performed.

Figure 3:
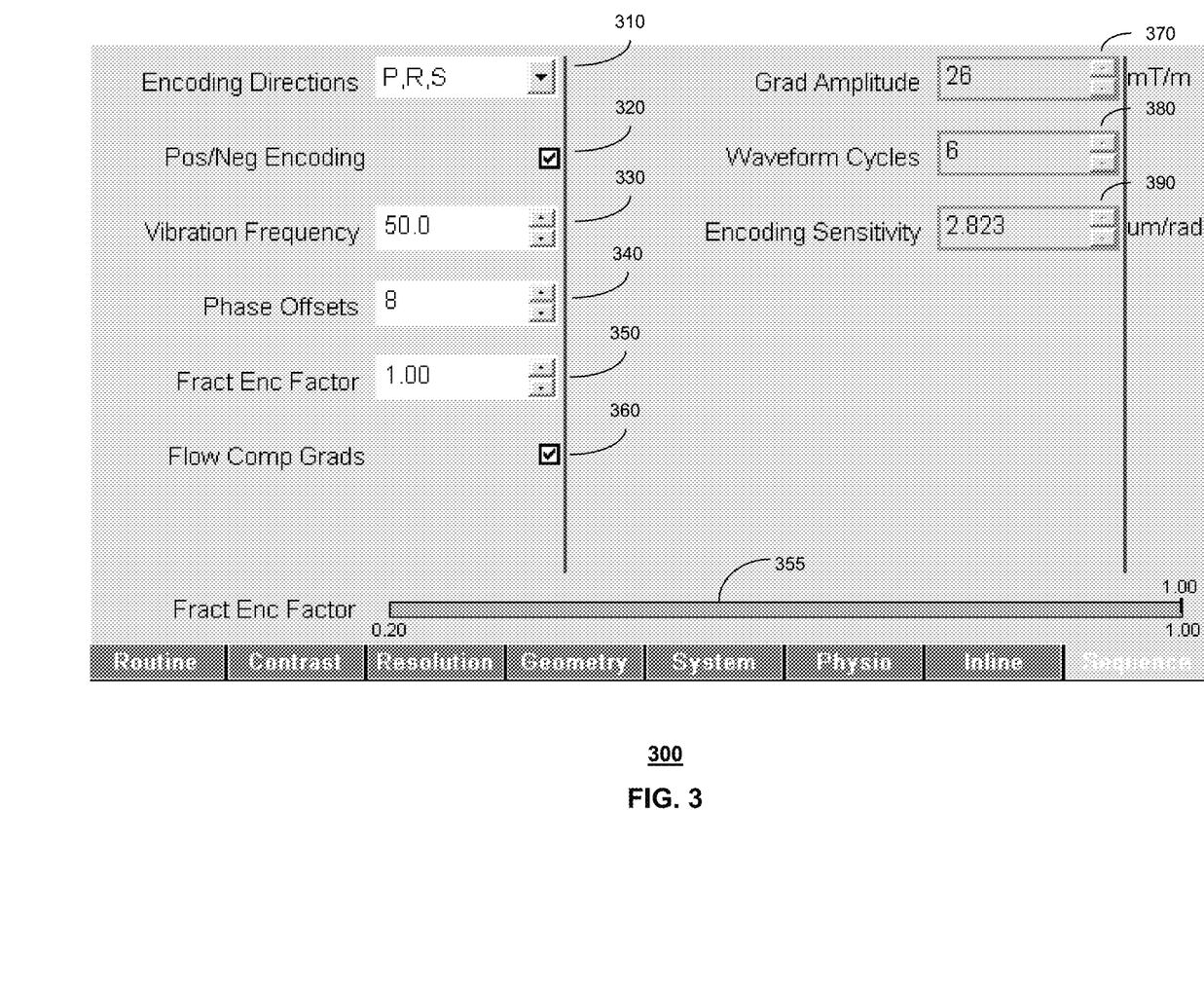
FIG. 3 is a screen capture diagram of MRE system settings.

FIG. 3 is an exemplary screen capture diagram 300 of system settings for acquiring brain MRE data. As shown in FIG. 3, MRE parameters can be selected, including encoding directions 310, MEG polarity 320, mechanical excitation (vibration) frequency 330, number of phase offsets 340, and fractional encoding factor 350, MEG shape 360, and MEG strength 370. A description of these MRE parameters are set forth above. Also shown in FIG. 3 are waveform cycles 380 and encoding sensitivity 390, which are not user selectable parameters.

As shown in FIG. 3, the MRE parameter set for imaging the tissue includes: three encoding directions; reversed polarity gradient; 50 Hz vibration frequency; eight phase offsets; 1.0 fractional encoding; flow-compensated gradient shape; and maximum gradient strength (26 mT/m). The checkbox for MEG polarity 320 chooses between positive polarity, and reverse (positive/negative) polarity. The checked checkbox for MEG polarity 320 indicates selection of a reverse (positive/negative) polarity. A fractional encoding factor bar graph 355 illustrates the MEG length relative to base MEG length, as described above. The checkbox for MEG shape 360 chooses between bipolar MEG shape and flow compensated shape. The checked checkbox for MEG shape 360 indicates selection of a flow-compensated MEG shape.

The system uses the selected MRE parameters to calculate the number of waveform cycles 380 that are applied during each EPI scan. As shown in FIG. 3, six cycles of mechanical agitation (120 ms) are required to readout a single EPI slice. The system also calculates an encoding sensitivity 390 for converting phase values to displacement magnitude, in this example, 2.823 um per radian.

Figure 4:
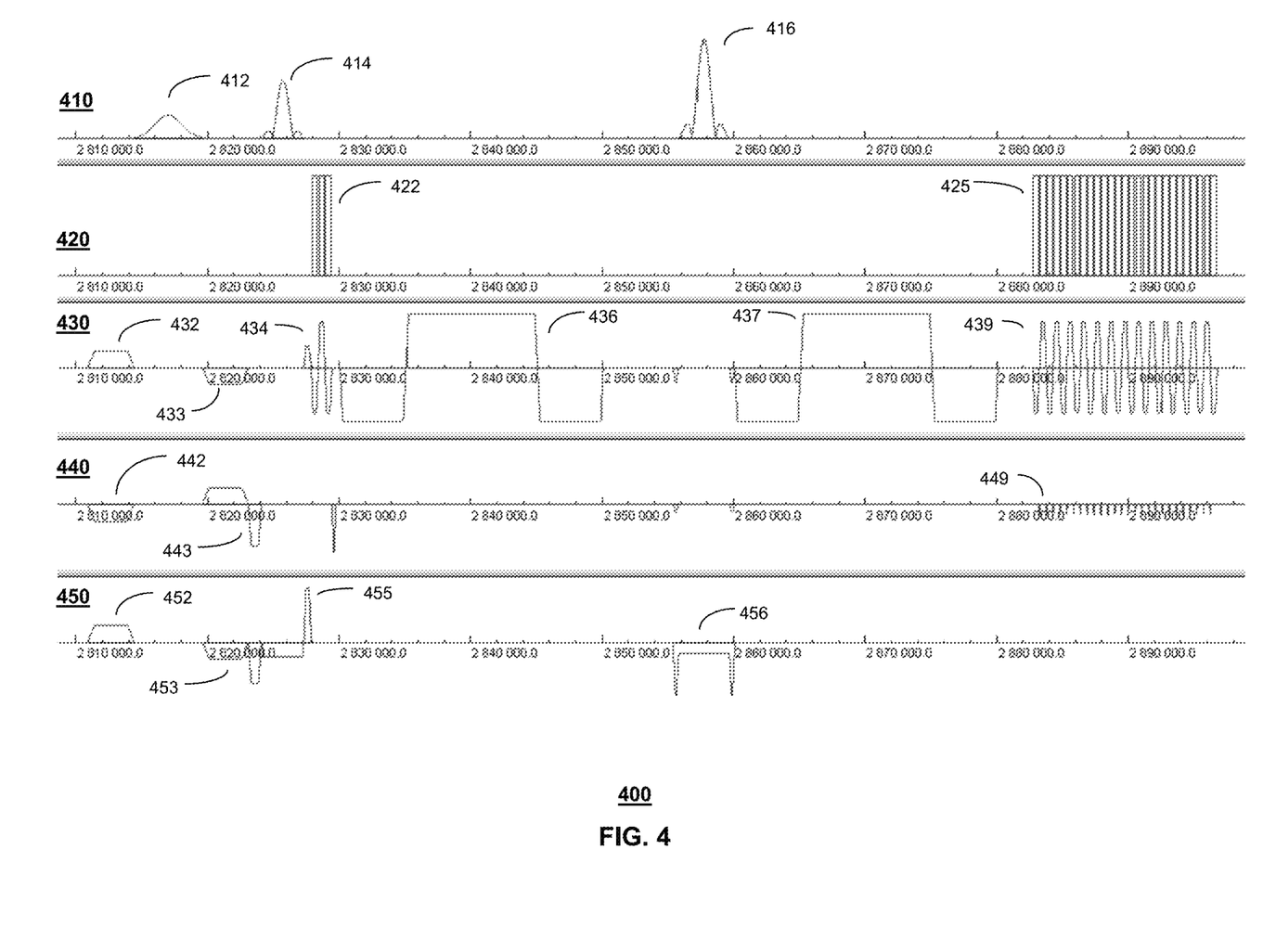
FIG. 4 is a timing diagram that illustrates an exemplary spin echo-planar imaging magnetic resonance gradient sequence for MRE.

FIG. 4 is an exemplary timing diagram that illustrates an exemplary spin echo EPI MEG sequence 400 for MRE used in practice for acquiring brain MRE data. The parameters were chosen to achieve a 3 mm isotropic resolution in less than 5 minutes while using a parallel imaging reduction factor, R=3. The full set of parameters used to generate the MEG sequence include:

| Parameter | Value |
| --- | --- |
| Axial FOV | 240 mm |
| Slice Matrix | 80 × 80 |
| # of Slices | 48 (3 mm thick) |
| Parallel Imaging Reduction | 3X (GRAPPA) |
| TE | 64.0 ms |
| TR | 4800 ms |
| Encoding Directions | +/−X, +/−Y, +/−Z |
| ME Frequency | 50 Hz |
| Phase Offsets | 8 |
| Fractional Encoding Factor | 1.0 |
| MEG Shape | Flow-compensated |
| MEG Strength | Maximum |
| MEG Polarity | Reversed |

The pulse sequence illustrated in FIG. 4 will acquire a sample magnetic resonance image in the X encoding direction at one particular phase offset. As illustrated in FIG. 4, the x-axis illustrates timing values (in microseconds), with each major tick mark representing hundredths of a second, and minor tick marks occurring every 2 milliseconds. Row 410 comprises RF excitation signals. Fat saturation RF pulse 412 is a short duration radio frequency pulse tuned to the resonant frequency of fat tissue. The fat saturation RF pulse 412 suppresses signals from subcutaneous fat tissue. RF excitation pulse 414 is a sinc pulse having a frequency that matches the slice-selection gradient frequency perpendicular to the desired slice that excites protons in the slice. Refocusing RF pulse 416 reverses the dephasing process due to spin precession, thereby helping to form the echo signal. The time between the RF excitation pulse 414 and the refocusing RF pulse 416 is half (32 ms) of the spin-echo time TE (64 ms).

Row 420 comprises data readout pulses. Reference numeral 422 indicates the acquisition of EPI phase correction k-space lines. Reference numeral 425 indicates the acquisition of EPI k-space lines. The k-space lines are acquired at around the TE, i.e., 64 ms from the RF excitation pulse 414.

Row 430 comprises frequency encoding (X) directional gradient signals. Reference numeral 432 and reference numeral 433 indicates gradient pulses for fat saturation. EPI readout gradients 434 are present for acquisition of k-space phase correction lines. MEG pulse 436 indicates the portion of the motion gradient before the refocusing RF pulse 416. MEG pulse 437 indicates the portion of the MEG after the refocusing RF pulse 416. In this MEG sequence, MEG pulses 436 and 437 are separated by a half cycle gap (10 ms) of the vibration frequency (50 Hz). EPI readout gradients 439 are present for acquisition of k-space lines. The MEG pulses 436 and 437 occur between the EPI readout gradients 434 and 439, which are defined by TE. As observed from the timeline, increasing the MEG length of MEG pulses 436 and 437, while maintaining the gap between them would require more room on the timeline. In other words, TE would have to be increased to accommodate a greater MEG pulse length.

Row 440 comprises phase encoding (Y) directional gradient signals. Reference numeral 442 and reference numeral 443 indicates gradient pulses for fat saturation. Reference numeral 449 indicates blipped gradients for adjusting k-space lines being acquired.

Row 450 comprises slice-selection (Z) directional gradient signals. Reference numeral 452 and reference numeral 453 indicate gradient pulses for fat saturation. Reference numeral 455 indicates an excitation slice-selection gradient and rephaser pulse. Reference numeral 456 indicates a refocusing slice-selection gradient pulse.

Figure 5:
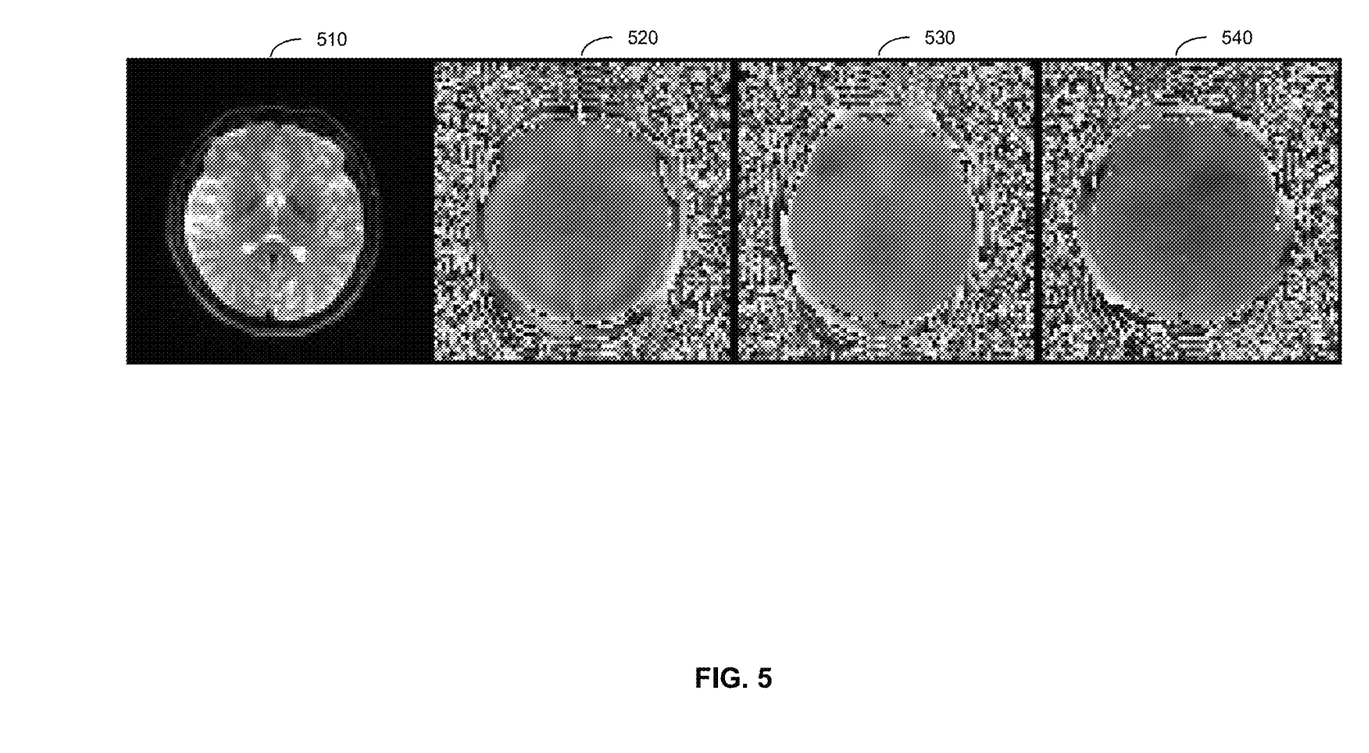
FIG. 5 illustrates images of a brain acquired during application of the exemplary spin echo-planar imaging magnetic resonance gradient sequence for MRE of FIG. 4.

FIG. 5 illustrates images of a brain acquired during application of the exemplary spin echo-planar imaging magnetic resonance gradient sequence for MRE of FIG. 4. Four images are shown in FIG. 5, including a low resolution magnetic resonance imaging (MRI) of brain 510, and three magnetic resonance elastographic images of the brain tissue in this slice for motion in the X direction 520, the Y direction 530, and the Z direction 540.

Figure 6:
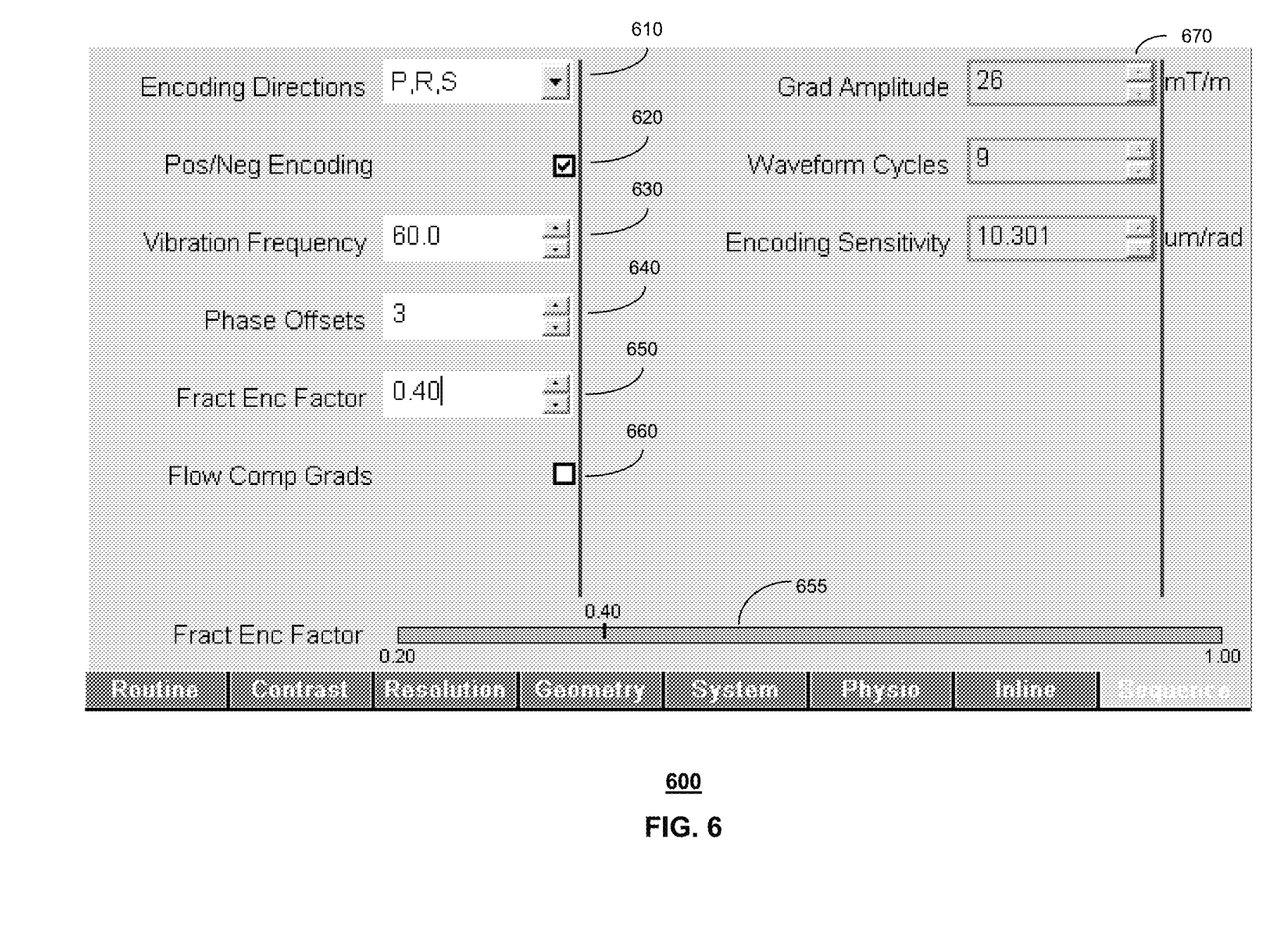
FIG. 6 is a screen capture diagram of MRE system settings.

FIG. 6 is an exemplary screen capture diagram 600 of system settings for acquiring liver MRE data. As shown in FIG. 6, MRE parameters can be selected, including encoding directions 610, MEG polarity 620, mechanical excitation (vibration) frequency 630, number of phase offsets 640, and fractional encoding factor 650, MEG shape 660, and MEG strength 670. A description of these MRE parameters are set forth above. As shown in FIG. 6, the MRE parameter set used for the liver includes: three encoding directions; reversed polarity gradient; three phase offsets; 60 Hz vibration frequency; 0.4 fractional encoding; a bipolar gradient shape; and maximum gradient strength (26 mT/m). The checked checkbox for MEG polarity 620 indicates selection of a reverse (positive/negative) polarity. A fractional encoding factor bar graph 655 illustrates the MEG length relative to base MEG length. The unchecked checkbox for MEG shape 660 indicates selection of a bipolar MEG shape.

Figure 7:
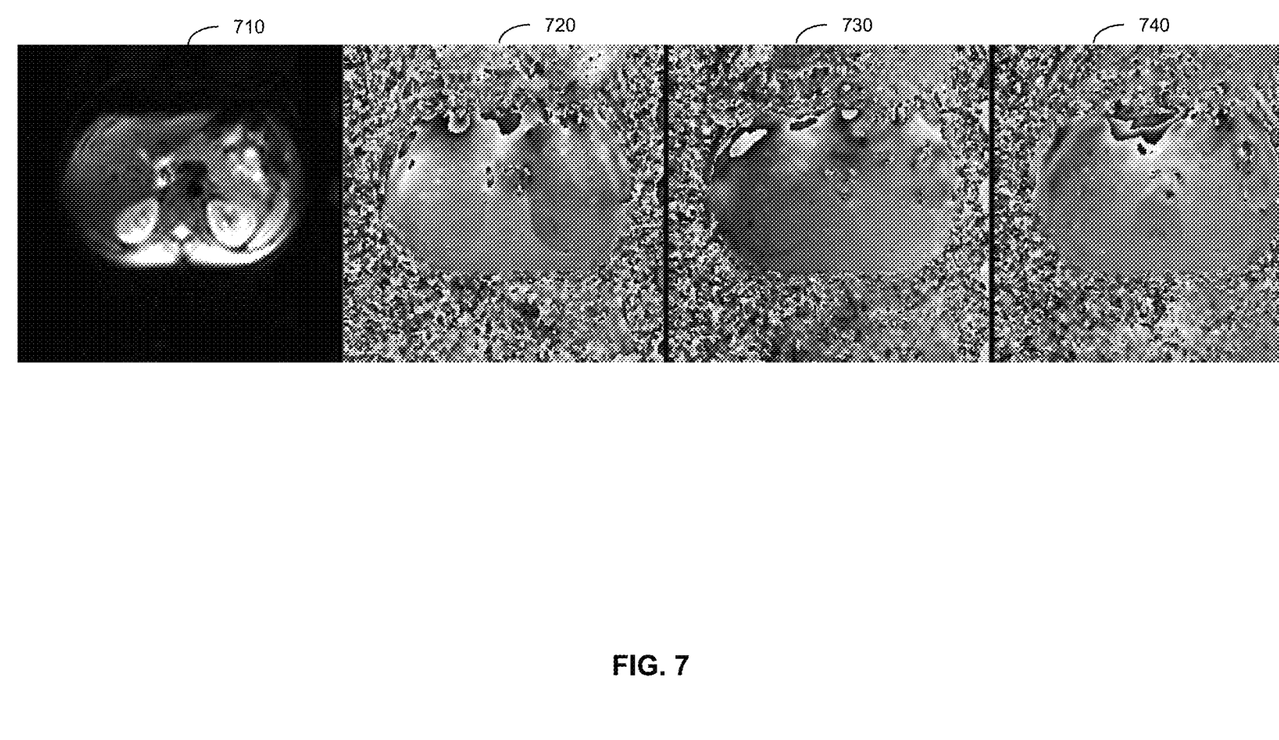
FIG. 7 illustrates images of a liver acquired during application of the exemplary spin echo-planar imaging magnetic resonance gradient parameters of FIG. 6.

FIG. 7 illustrates images of a liver acquired during application of the exemplary spin echo-planar imaging magnetic resonance gradient sequence generated from the MRE parameters of FIG. 6. Four images are shown in FIG. 7, including a low resolution magnetic resonance imaging (MRI) of the liver 710, and three magnetic resonance elastographic images of the liver tissue in this slice for motion in the X direction 720, the Y direction 730, and the Z direction 740.

Figure 8:
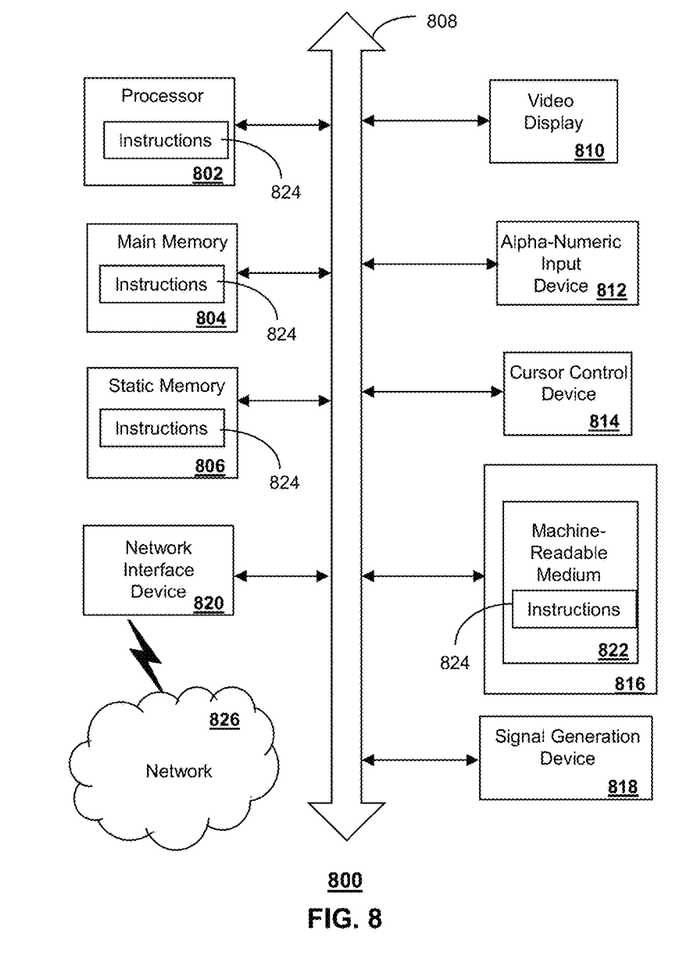
FIG. 8 depicts an exemplary diagrammatic representation of a machine in the form of a computer system.

FIG. 8 depicts an exemplary diagrammatic representation of a machine in the form of a computer system 800 within which a set of instructions, when executed, may cause the machine to perform any one or more of the methods describe above. One or more instances of the machine can operate, for example, as the computer 140 of FIG. 1. In some embodiments, the machine may be connected (e.g., using a network 826) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 800 may include a processor 802 (e.g., a controller, a central processing unit (CPU), a graphics processing unit (GPU, or both)), a main memory 804 and a static memory 806, which communicate with each other via a bus 808. The computer system 800 may further include a display unit 810 (e.g., a liquid crystal display (LCD), a flat panel, or a solid state display. The computer system 800 may include an input device 812 (e.g., a keyboard), a cursor control device 814 (e.g., a mouse), a disk drive unit 816, a signal generation device 818 (e.g., a speaker or remote control) and a network interface device 820. In distributed environments, the embodiments described in the subject disclosure can be adapted to utilize multiple display units 810 controlled by two or more computer systems 800. In this configuration, presentations described by the subject disclosure may in part be shown in a first of the display units 810, while the remaining portion is presented in a second of the display units 810.

The disk drive unit 816 may include a tangible computer-readable storage medium 822 on which is stored one or more sets of instructions 824 (e.g., software) embodying any one or more of the methods or functions described herein, including those methods illustrated above. The instructions 824 may also reside, completely or at least partially, within the main memory 804, the static memory 806, and/or within the processor 802 during execution thereof by the computer system 800. The main memory 804 and the processor 802 also may constitute tangible computer-readable storage media.

Dedicated hardware implementations including, but not limited to, application specific integrated circuits, programmable logic arrays and other hardware devices that can likewise be constructed to implement the methods described herein. Application specific integrated circuits and programmable logic array can use downloadable instructions for executing state machines and/or circuit configurations to implement embodiments of the subject disclosure. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the operations or methods described herein are intended for operation as software programs or instructions running on or executed by a computer processor or other computing device, and which may include other forms of instructions manifested as a state machine implemented with logic components in an application specific integrated circuit or field programmable array. Furthermore, software implementations (e.g., software programs, instructions, etc.) can include, but not limited to, distributed processing or component/object distributed processing, parallel processing, or virtual machine processing can also be constructed to implement the methods described herein. It is further noted that a computing device such as a processor, a controller, a state machine or other suitable device for executing instructions to perform operations or methods may perform such operations directly or indirectly by way of one or more intermediate devices directed by the computing device.

While the tangible computer-readable storage medium 822 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure. The term "non-transitory" as in a non-transitory computer-readable storage includes without limitation memories, drives, devices and anything tangible but not a signal per se.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information, including processor executable instructions. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, and HTTP) represent examples of the state of the art. Such standards are from time-to-time superseded by faster or more efficient equivalents having essentially the same functions. Wireless standards for device detection (e.g., RFID), short-range communications (e.g., Bluetooth®, WiFi, and ZigBee®), and long-range communications (e.g., WiMAX, GSM, CDMA, and LTE) can be used by computer system 800.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. The exemplary embodiments can include combinations of features and/or steps from multiple embodiments. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, can be used in the subject disclosure. In one or more embodiments, features that are positively recited can also be excluded from the embodiment with or without replacement by another component or step. The steps or functions described with respect to the exemplary processes or methods can be performed in any order. The steps or functions described with respect to the exemplary processes or methods can be performed alone or in combination with other steps or functions (from other embodiments or from other steps that have not been described).

Less than all of the steps or functions described with respect to the exemplary processes or methods can also be performed in one or more of the exemplary embodiments. Further, the use of numerical terms to describe a device, component, step or function, such as first, second, third, and so forth, is not intended to describe an order or function unless expressly stated so. The use of the terms first, second, third and so forth, is generally to distinguish between devices, components, steps or functions unless expressly stated otherwise. Additionally, one or more devices or components described with respect to the exemplary embodiments can facilitate one or more functions, where the facilitating (e.g., facilitating access or facilitating establishing a connection) can include less than every step needed to perform the function or can include all of the steps needed to perform the function.

In one or more embodiments, a processor (which can include a controller or circuit) has been described that performs various functions. It should be understood that the processor can be multiple processors, which can include distributed processors or parallel processors in a single machine or multiple machines. The processor can be used in supporting a virtual processing environment. The virtual processing environment may support one or more virtual machines representing computers, servers, or other computing devices. In such virtual machines, components such as microprocessors and storage devices may be virtualized or logically represented. The processor can include a state machine, application specific integrated circuit, and/or programmable gate array including a Field PGA. In one or more embodiments, when a processor executes instructions to perform "operations", this can include the processor performing the operations directly and/or facilitating, directing, or cooperating with another device or component to perform the operations.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

What is claimed is:

1. A non-transitory, computer-readable storage medium, comprising executable instructions that, when executed by a processor, causes the processor to perform operations, comprising:
   applying a vibration to human tissue;
   acquiring a sample magnetic resonance elastographic image of the human tissue subject to the vibration using a motion encoded gradient sequence;
   measuring a contrast to noise ratio of the sample magnetic resonance elastographic image;
   adjusting magnetic resonance elastographic parameters of motion encoding gradient pulses in the motion encoded gradient sequence to increase the contrast to noise ratio measured, resulting in adjusted magnetic resonance elastographic parameters; and
   generating an updated motion encoded gradient sequence using the adjusted magnetic resonance elastographic parameters that produces an increased contrast to noise ratio.

2. The non-transitory, computer-readable storage medium of claim 1, wherein adjusted magnetic resonance elastographic parameters comprises reducing a motion encoding gradient pulse length.

3. The non-transitory, computer-readable storage medium of claim 2, wherein the adjusted magnetic resonance elastographic parameters comprise a different motion encoding gradient pulse shape.

4. The non-transitory, computer-readable storage medium of claim 3, wherein the adjusted magnetic resonance elastographic parameters comprise a different motion encoding gradient pulse strength.

5. The non-transitory, computer-readable storage medium of claim 4, wherein adjusted magnetic resonance elastographic parameters comprises a reversed polarity motion encoding gradient pulse.

6. The non-transitory, computer-readable storage medium of claim 2, wherein the adjusted magnetic resonance elastographic parameters comprise a fractional encoding factor that reduces the motion encoding gradient pulse length, and adjusting the fractional encoding factor increases a signal to noise ratio, wherein improving the signal to noise ratio increases the contrast to noise ratio.

7. The non-transitory, computer-readable storage medium of claim 1, wherein adjusting a vibration frequency of the vibration increases a signal to noise ratio, wherein improving the signal to noise ratio increases the contrast to noise ratio.

8. The non-transitory, computer-readable storage medium of claim 1, wherein adjusting the magnetic resonance elastographic parameters increases the contrast to noise ratio to 3 or more.

9. The non-transitory, computer-readable storage medium of claim 1, wherein the operations further comprise applying a short duration radio frequency pulse, wherein the short duration radio frequency pulse is tuned to a resonant frequency of fat tissue.

10. A device, comprising:
    a processor; and
    a memory that stores executable instructions that, when executed by the processor, causes the process or to perform operations, comprising:
      receiving image parameters for generating a plurality of magnetic resonance elastographic images of human tissue;
      setting magnetic resonance elastographic parameters of motion encoding gradient pulses based on an identified type of the human tissue;
      acquiring a sample image of the human tissue based on the image parameters and the magnetic resonance elastographic parameters;
      measuring a contrast to noise ratio of the sample image;
      determining whether the contrast to noise ratio exceeds a target contrast to noise ratio;
      adjusting the magnetic resonance elastographic parameters of the motion encoding gradient pulses in a motion encoded gradient sequence based on the contrast to noise ratio measured to increase the contrast to noise ratio, responsive to a determination that the contrast to noise ratio is below the target contrast to noise ratio;
      repeating the measuring, determining and adjusting operations until the contrast to noise ratio exceeds the target contrast to noise ratio; and
      generating the plurality of magnetic resonance elastographic images of the human tissue using the motion encoded gradient sequence with adjusted motion encoding gradient pulses.

11. The device of claim 10, wherein the magnetic resonance elastographic parameters include a fractional encoding factor, and the adjusting operation further comprises changing the fractional encoding factor to increase a signal to noise ratio, wherein increasing the signal to noise ratio increases the contrast to noise ratio.

12. The device of claim 10, wherein the magnetic resonance elastographic parameters include a vibration frequency, and the adjusting operation further comprises changing the vibration frequency to increase a signal to noise ratio, wherein increasing the signal to noise ratio increases the contrast to noise ratio.

13. The device of claim 10, wherein the magnetic resonance elastographic parameters include a number of phase offsets, and the adjusting operation further comprises changing the number of phase offsets to increase an image contrast, wherein increasing the image contrast increases the contrast to noise ratio.

14. The device of claim 10, wherein the magnetic resonance elastographic parameters include a motion encoding gradient pulse shape, and the adjusting operation further comprises changing the motion encoding gradient pulse shape to increase sensitivity to motion, wherein increasing the sensitivity to motion increases the contrast to noise ratio.

15. The device of claim 10, wherein the magnetic resonance elastographic parameters include a motion encoding gradient pulse strength, and the adjusting operation further comprises changing the motion encoding gradient pulse strength to prevent phase wrapping, wherein preventing phase wrapping increases the contrast to noise ratio.

16. The device of claim 10, wherein the magnetic resonance elastographic parameters include a motion encoding gradient pulse polarity, and the adjusting operation further comprises changing the motion encoding gradient pulse polarity to a reversed polarity direction, wherein the reversed polarity direction increases image contrast that increases the contrast to noise ratio.

17. A method, comprising:
acquiring, by a system comprising a processor, a sample magnetic resonance image of elastically deformed human tissue;
measuring, by the system, a contrast to noise ratio of the sample magnetic resonance image;
adjusting, by the system, magnetic resonance elastographic parameters of motion encoding gradient pulses in a motion encoded gradient sequence based on the contrast to noise ratio measured to increase the contrast to noise ratio, responsive to a determination that the contrast to noise ratio is below a predetermined level; and
repeating, by the system, the measuring and adjusting until the contrast to noise ratio is above the predetermined level.

18. The method of claim 17, wherein adjusting the magnetic resonance elastographic parameters includes reducing a motion encoding gradient pulse length.

19. The method of claim 17, wherein adjusting the magnetic resonance elastographic parameters includes changing a motion encoding gradient pulse shape.

20. The method of claim 17, wherein adjusting the magnetic resonance elastographic parameters includes lowering a motion encoding gradient pulse strength.

* * * * *

UNITED STATES PATENT AND TRADEMARK OFFICE
CERTIFICATE OF CORRECTION

| | | |
|---|---|---|
| PATENT NO. | : 11,033,199 B2 | |
| APPLICATION NO. | : 15/193171 | |
| DATED | : June 15, 2021 | |
| INVENTOR(S) | : Johnson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1181 days.

Signed and Sealed this
Fourteenth Day of February, 2023

Katherine Kelly Vidal
*Director of the United States Patent and Trademark Office*